United States Patent

Kammerer et al.

[11] Patent Number: 5,769,862
[45] Date of Patent: Jun. 23, 1998

[54] TUBE KNOT APPLICATOR

[75] Inventors: Gene W. Kammerer, East Brunswick; Bruno Bufalini, Creskill; Royce Frederick, South Bound Brook; Chao Chen, Edison, all of N.J.

[73] Assignee: Ethicon, Inc., Somerville, N.J.

[21] Appl. No.: 635,448

[22] Filed: Apr. 19, 1996

Related U.S. Application Data

[63] Continuation of Ser. No. 401,754, Mar. 9, 1995, abandoned, which is a continuation of Ser. No. 92,400, Jul. 14, 1993, Pat. No. 5,454,820.

[51] Int. Cl.[6] ................................................. A61B 17/00
[52] U.S. Cl. ........................ 606/148; 606/144; 606/139
[58] Field of Search .................................. 606/139, 144, 606/145, 148, 140, 141; 112/169, 80.03

[56] References Cited

U.S. PATENT DOCUMENTS

| | | | |
|---|---|---|---|
| 2,614,564 | 10/1952 | Giaccaglia | 606/139 |
| 5,100,418 | 3/1992 | Yoon et al. | 606/139 |
| 5,226,908 | 7/1993 | Yoon | 606/140 |
| 5,318,578 | 6/1994 | Hasson | 606/139 |
| 5,391,176 | 2/1995 | De La Torre | 606/148 |

Primary Examiner—Jeffrey A. Schmidt
Attorney, Agent, or Firm—Emil Richard Skula

[57] ABSTRACT

A tube knot applicator for use in endosurgical procedures. The tube knot applicator has an elongated tube member having a distal end and a proximal end, as well as an axial passage therethrough. The tube member has slits for partially collapsing the distal end of the tube as well as a removable plug mounted in the distal end of the tube to prevent the distal end of the tube from collapsing by supporting the distal slitted end. A suture having at least one slip knot and at least one locking knot is mounted in the tube knot applicator with the knot tied about the collapsing distal end of the tube. A sleeve is mounted to the distal end of the tube knot applicator over the suture knot and the distal end.

20 Claims, 9 Drawing Sheets

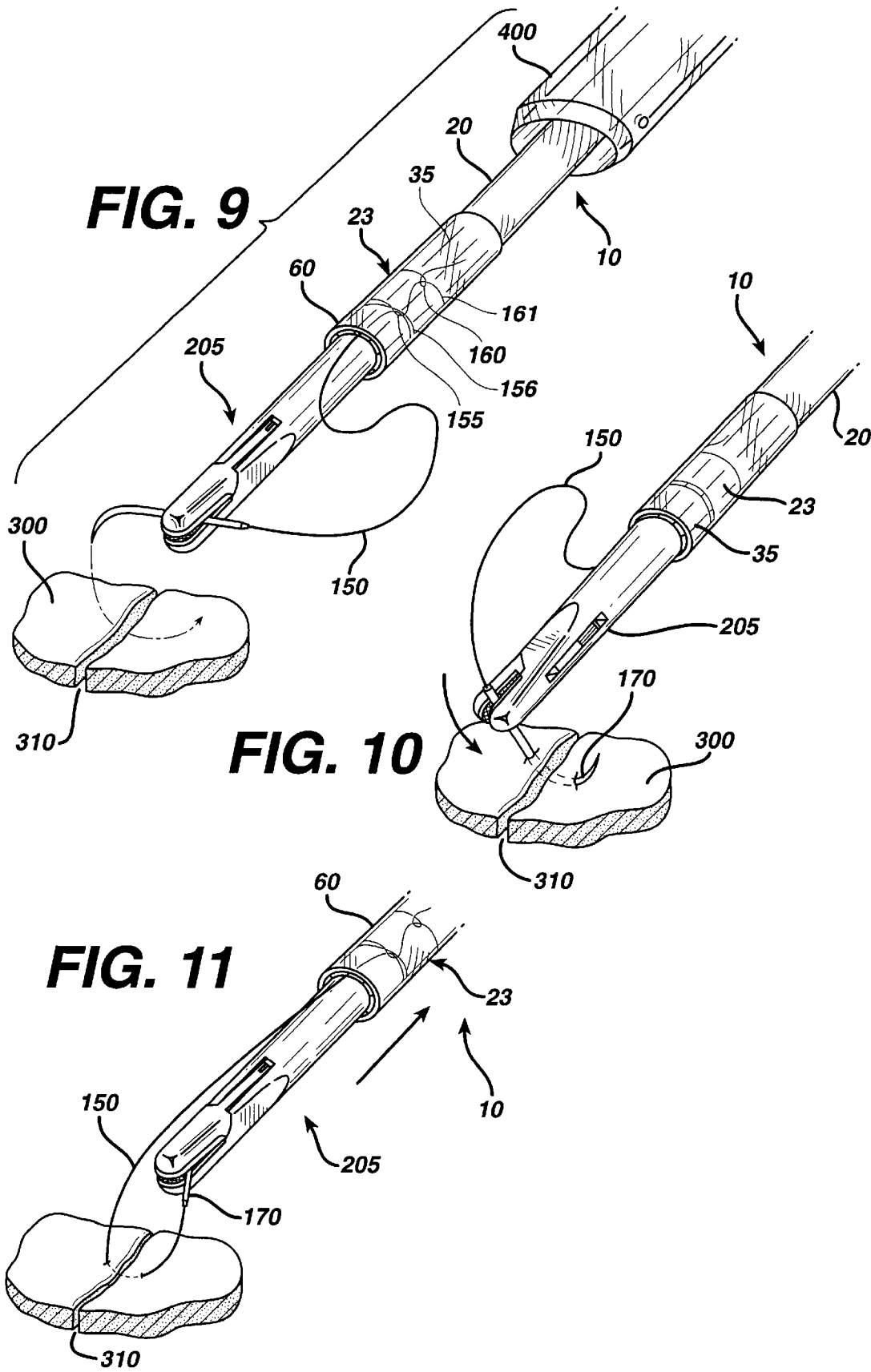

TUBE KNOT APPLICATOR

This is a continuation of application Ser. No. 08/401,754, filed Mar. 9, 1995 now abandoned, which is a continuation of Ser. No. 08/092,400 filed Jul. 14, 1995, now U.S. Pat. No. 5,454,820.

TECHNICAL FIELD

The field of art to which this invention relates is endoscopic surgical instruments, in particular, endoscopic suturing devices.

BACKGROUND OF THE INVENTION

Endoscopic surgical (endosurgical) procedures are receiving wide acceptance in the medical community, as well as among the patient population. The term endoscopic as used herein is meant to refer to minimally invasive surgical techniques, including endoscopy, laparoscopy, thoracoscopy, and arthroscopy. The advantages of endoscopic surgical techniques include reduced post-operative recuperation period, reduced hospital stay, decreased pain, decreased scarring, and a decrease in the length of the operative procedure.

Endoscopic surgical techniques are typically performed by inserting conventional trocars into a patient's body cavity in order to access a particular surgical site, e.g., the gall bladder. Conventional trocars typically consist of an elongated obturator having a piercing point which is concentrically mounted in a conventional trocar cannula. Conventional trocar cannulas typically consist of an elongated hollow tube mounted in a hollow handle. The trocars are inserted into the body cavity and positioned proximate to the surgical site. Then, the trocar obturators are removed, leaving the trocar cannulas as pathways to the body cavity. A conventional endoscope is typically inserted into one of the trocar cannulas. The remaining trocar cannulas are used as pathways to and from the body cavity for instruments and the like.

Numerous endoscopic instruments have been developed for use in endoscopic procedures, including surgical staplers, cutters, graspers, manipulators and the like. In addition, endoscopic suturing devices have been developed and are available for the surgeon. One type of conventional endoscopic suturing device typically consists of an elongated cannula, having an internal axial passage. A suture is typically threaded through the axial passage and extends through and out of the distal end of the cannula. A conventional surgical needle is typically mounted to the end of the distally extending suture. Typically, a pre-tied loop and knot have been emplaced in the distally extending section of the suture. The cannula is typically inserted through a trocar site and the needle and suture are then manipulated using endoscopic needle holders and graspers. Although conventional endoscopic suturing devices are available there may be disadvantages associated with their use. For example, two additional trocar cannulas (in addition to the trocar cannula needed for the suture device) are typically necessary for needle graspers to manipulate the needle and suture. It is also known that with some conventional endoscopic suturing devices it may be difficult for the surgeon to manipulate the needle and suture.

There is a continuing need in this art for new endoscopic suturing devices, which are easily used by the surgeon when performing endoscopic suturing.

DISCLOSURE OF THE INVENTION

Therefore, it is an object of the present invention to provide a novel endoscopic suturing device, which provides improved knot tying capability when used in an endosurgical procedure.

It is a further object of the present invention to provide an endoscopic suturing device which eliminates the need for a second trocar cannula for the needle grasper instruments.

Accordingly, a tube knot applicator is disclosed. The tube knot applicator comprises a tube having a distal end and a proximal end, as well as an axial passage therethrough. The tube has means for partially collapsing the distal end of the tube, as well as a removable plug means mounted in the distal end of the tube to prevent the distal end of the tube from collapsing by counteracting the tube collapsing means. An optional trocar cannula mounting plate having a hole therethrough may be mounted to the tube. Sleeve means having an inner surface and an outer surface are mounted to the distal end of the tube.

Another aspect of the present invention is a tube knot applicator having an elongated tube. The tube has a distal end, a proximal end, and an axial passage therethrough. The tube has an inner surface and an outer surface. The tube has means for partially collapsing the distal end of the tube. The means preferably comprise a plurality of longitudinal slots extending proximally from the distal end of the tube. An optional trocar cannula mounting plate having a passage therethrough may be mounted to the tube. Removable plug means are mounted in the distal end of the tube to prevent the distal end of the tube from collapsing. Sleeve means having an inner surface and an outer surface are mounted to the tube over the distal end of the tube. A suture is threaded through the tube. At least one pre-tied knot formed in the suture and at least one suture loop are mounted about the distal end of the tube and maintained between the outer surface of the distal end of the tube and the inner surface of the sleeve means. Optional sealing means are mounted to the proximal end of the tube.

Yet another aspect of the present invention, is a method of using the above-described tube knot applicator in an endoscopic surgical procedure.

Yet a further aspect of the present invention is a tube knot applicator which comprises a tube having a distal end and a proximal end, as well as an axial passage therethrough. The tube has means for partially collapsing the distal end of the tube, as well as a removable plug means mounted in the distal end of the tube to prevent the distal end of the tube from collapsing by counteracting the tube collapsing means. An optional trocar cannula mounting plate having a hole therethrough may be mounted to the tube.

Yet another aspect of the present invention is a tube knot applicator having an elongated tube. The tube has a distal end, a proximal end, and an axial passage therethrough. The tube has an inner surface and an outer surface. The tube has means for partially collapsing the distal end of the tube. The means preferably comprise a plurality of longitudinal slots extending proximally from the distal end of the tube. An optional trocar cannula mounting plate having a passage therethrough may be mounted to the tube. Removable plug means are mounted in the distal end of the tube to prevent the distal end of the tube from collapsing. A suture is threaded through the tube. At least one pre-tied knot formed in the suture and at least one suture loop are mounted about the distal end of the tube. Optional sealing means are mounted to the proximal end of the tube.

The endoscopic tube knot applicators of the present invention have many advantages. The pre-tied suture knots and loops are protected by a sleeve, in a preferred embodiment, when being inserted through a trocar cannula. The formation of knots is simplified. Merely pulling the needle and a grasping instrument holding the needle proximally causes the knot or knots to slip off of the distal end of the tube knot applicator and onto the suture. The needle is easily drawn through the suture loops by merely pulling the needle back into the distal end of the tube knot applicator. In addition, a needle grasper instrument may be inserted through the same trocar cannula in which the tube knot applicator has been inserted (actually through the tube knot applicator), thereby eliminating the need for an additional trocar cannula for the needle grasper.

Other features and advantages of the invention will become more apparent from the following description and accompanying drawings.

DESCRIPTION OF THE DRAWINGS

FIG. 1A is a perspective view of an alternate embodiment of the tube knot applicator or the present invention having a polyhedral cross-section.

FIG. 1B is a perspective view of an alternate embodiment of the tube knot applicator or the present invention having a rectangular cross-section.

FIG. 9 is a perspective view of a endoscopic needle grasper extending through the tube knot applicator of FIG. 8 prior to inserting the needle through tissue to close an incision in the tissue.

FIG. 10 is a perspective view showing the distal sections of the needle grasper and tube knot applicator of FIG. 9 wherein the needle is inserted through both sides of the tissue surrounding the incision.

FIG. 11 is a partial perspective view showing the needle grasper grasping the needle and pulling the suture proximally and about the incision as the needle grasper is retracted proximally into the tube knot applicator.

BEST MODE FOR CARRYING OUT THE INVENTION

Figure 1:
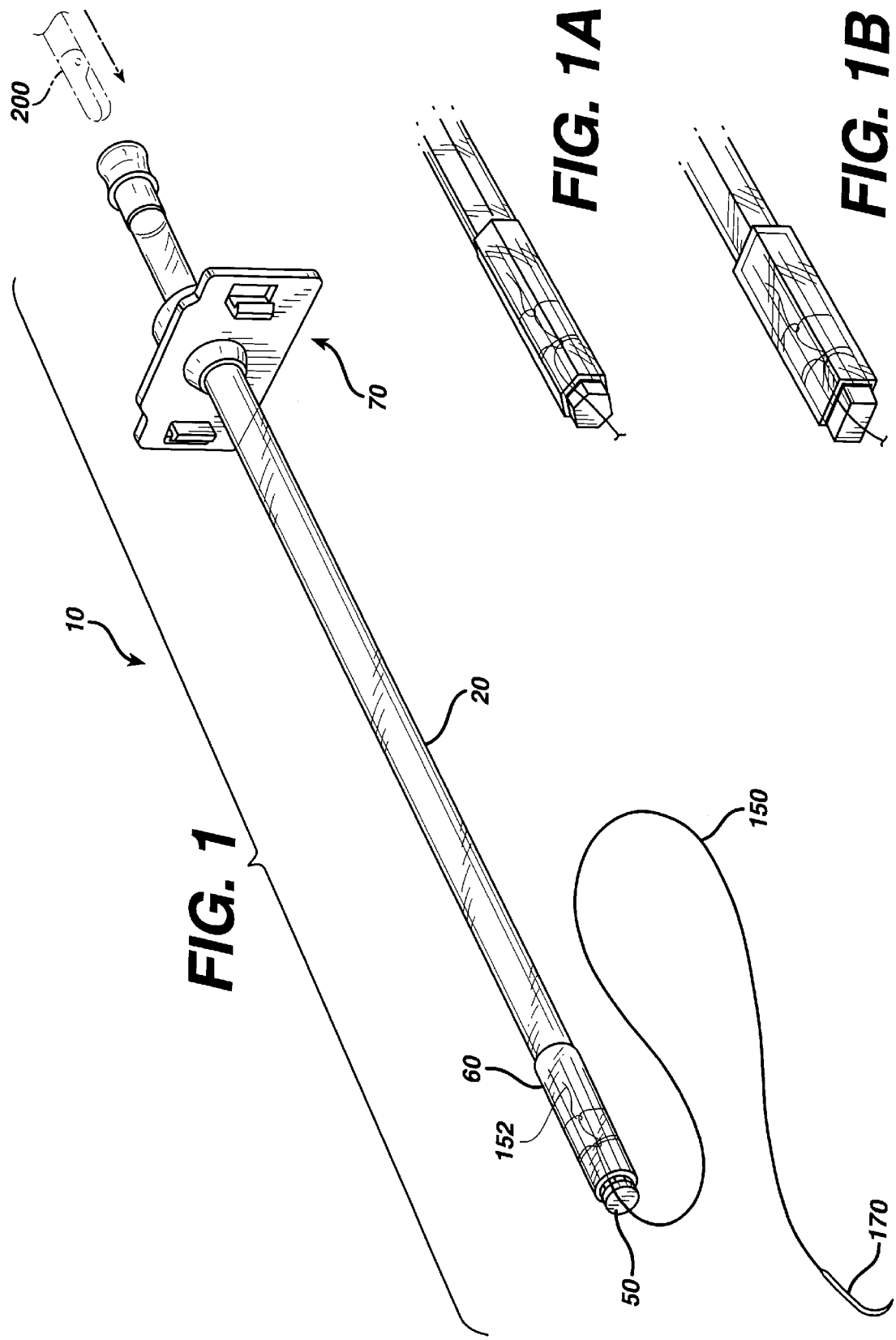
FIG. 1 is a perspective view of the tube knot applicator of the present invention with a surgical suture and surgical needle mounted prior to use.
Figure 2:
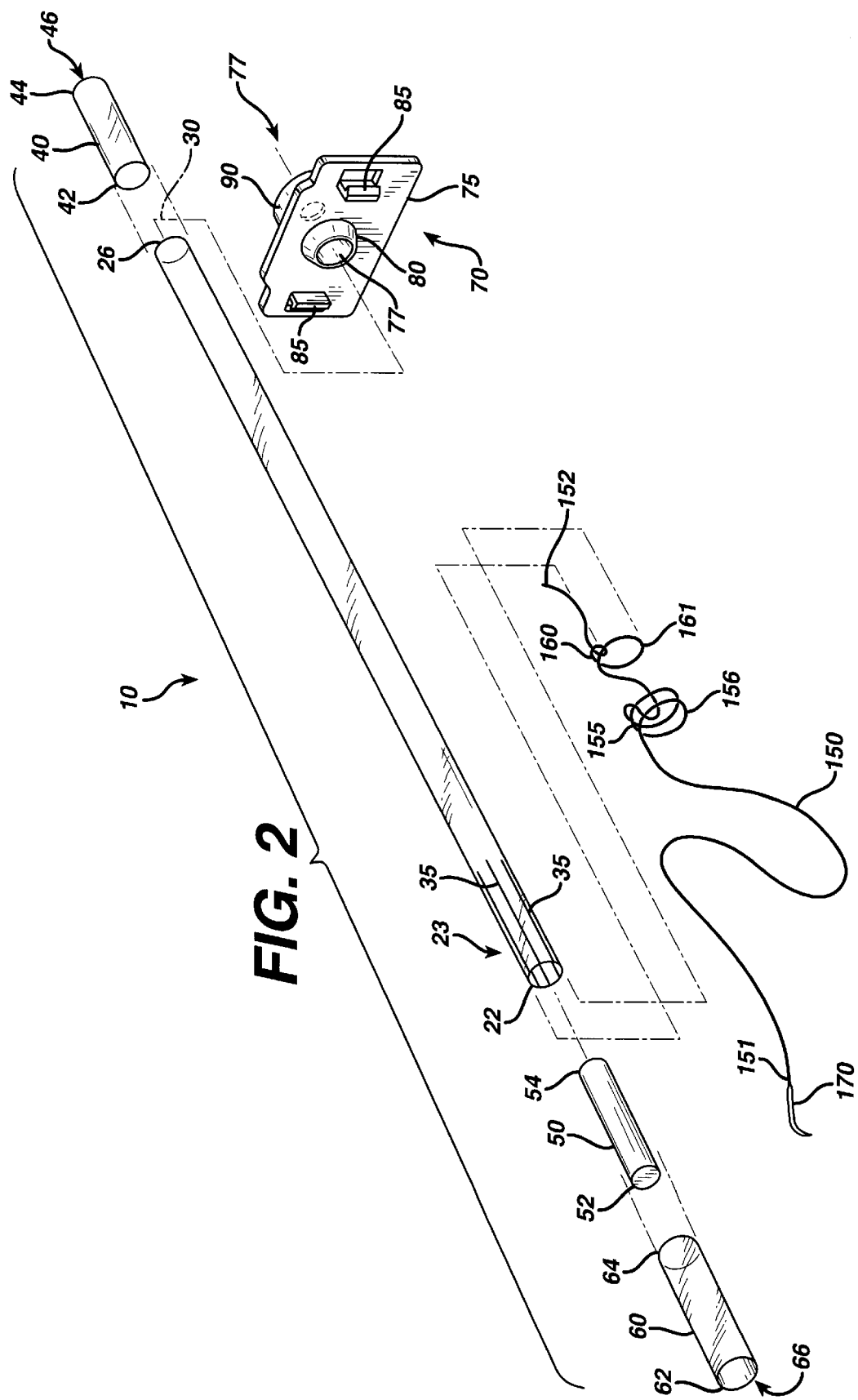
FIG. 2 is an exploded perspective view of the tube knot applicator of the present invention also showing a surgical needle and suture having pre-tied knots and loops.
Figures 5, 6, 7:
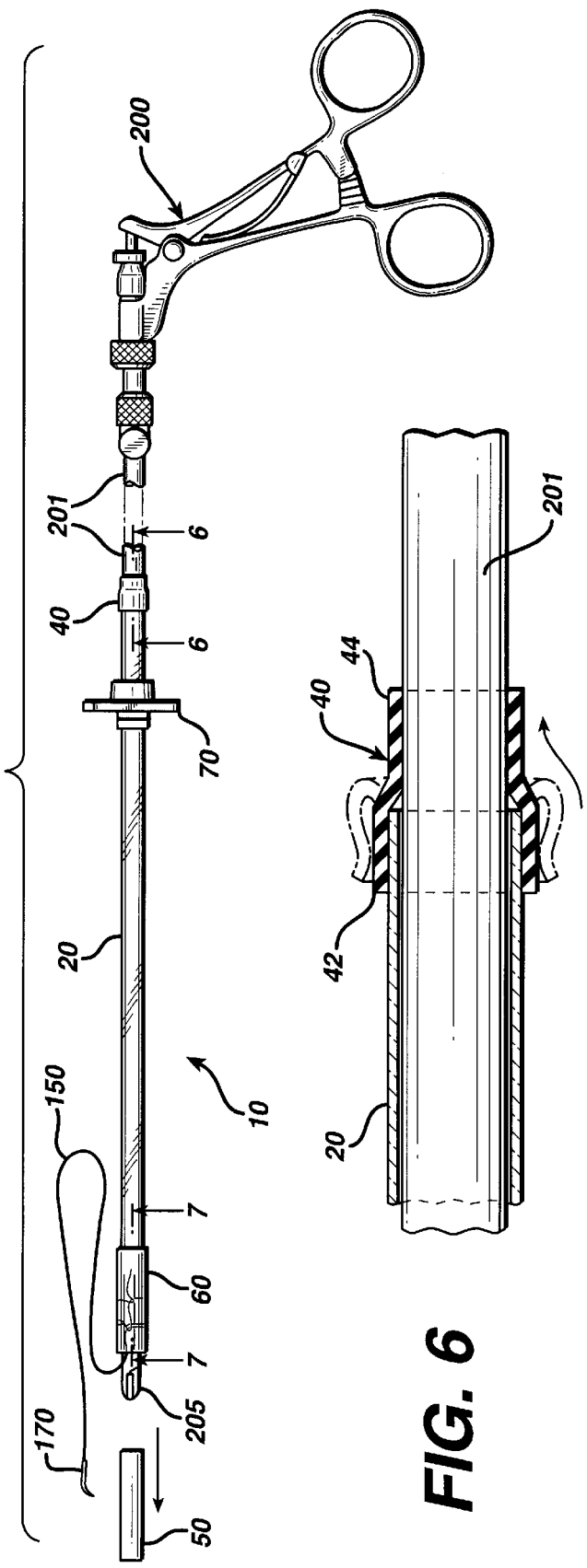
FIG. 5 is a side view of the tube knot applicator of FIG. 1 with an endoscopic needle grasper inserted through the tube and with the distal end of the grasper extending out of the distal end of the tube and also showing the plug member displaced from the distal end of the tube.
FIG. 6 is a partial cut-away view taken along View Line 6—6 showing the resilient sleeve seal in contact with the outer surface of the needle grasper of FIG. 5.
FIG. 7 is a partial cutaway view along View Line 7—7, showing the distal end of the tube knot applicator of FIG. 5, with the distal end of the needle grasper extending through and out of the distal end, thereby preventing the distal end of the tube from collapsing; also illustrated are the suture loops and knots positioned between the outer surface of the distal end of the tube and the inner surface of the sleeve.

Referring to FIGS. 1, 2 and 5, the tube knot applicator 10 of the present invention is illustrated in perspective and side views. Tube knot applicator 10 is seen to have elongated tube 20. The tube 20 has distal end 22 and proximal end 26 and distal end section 23. Although it is preferred that tube 20 have a circular cross-section, tube 20 may have any geometric cross-section including triangular, square, elliptical, rectangular, polyhedral, semicircular, equivalents thereof and combinations thereof.

The tube 20 is also seen to have axial passage 30 and at least two distal slits 35 in distal end section 23. The number of slits will be sufficient to effectively allow distal end section 23 to collapse when not supported internally. The number of slits will vary depending upon the tube configuration, wall thickness, material of construction and the like. The number of slits for a tube having a circular cross-section is typically at least about one and preferably about six to about eight. The slits 35 extend through the wall of tube 20. The slits 35 may be formed by conventional methods including cutting, molding and the like. The slits 35 are sufficiently long to effectively allow distal end section 23 to collapse. If desired, the slits although preferably longitudinal may be combined with slits which are partially circumferential.

The distal end section 23 with slits 35 may also be replaced by equivalent collapsing means such as an elastic or resilient or fabric tubular member mounted to the distal end 22 of tube 20 or any equivalent member which collapses when unsupported.

Mounted to the proximal end 26 of the tube 20 is the optional resilient sleeve 40 (See FIGS. 1, 5 and 6). Resilient sleeve 40 is seen to have distal end 42, proximal end 44 and axial passage 46. The resilient sleeve 40 is preferably made from a polymeric material having sufficient elasticity and resilience to effectively stretch over and seal a tubular member having a larger outside diameter. The distal end 42 of resilient sleeve 40 is elastically stretched and placed over the proximal end 26 of tube 20. The distal end 42 remains engaged to proximal end 26 by frictional contact but may be mounted using mechanical fasteners, adhesives and the like if desired. The inner diameter of sleeve 40 will typically be smaller than the outer diameter of tube 20. Other equivalent sealing means may be mounted to tube 20 including conventional seals such as clamps, gaskets seals, mechanical connectors and the like.

The tubular sleeve 40 serves several functions. It provides a substantially fluid tight seal between a needle grasper inserted into the tube 20 and the inner surface of the tube 20 thereby assisting in maintaining the insufflation of a body cavity or joint. Tubular sleeve 40 also holds needle grasper 200 in tube 20 in a specific alignment with respect to tube 20 so that grasper 200 does not inadvertently slide within tube 20.

Referring also to FIG. 7, the tubular sleeve 60 is seen to be a tubular member having a distal end 62, a proximal end 64 and an axial passage 66. The inner diameter of tubular sleeve 66 will be sufficiently large to effectively slide over the exterior of tube 20, that is, the inner diameter of tube 60 will be greater than the outer diameter of tube 20. The annular gap 68 between the outer diameter of tube 20 and the inner diameter of tubular sleeve 60 will be sufficiently large to effectively contain the suture loops and knots 155 and 160, but sufficiently small to effectively provide for contact between the suture loops and/or knots 155 and 160 and the exterior of tube 20 and the interior of tube 60 and to thereby prevent them from prematurely sliding off of the collapsible end 23 of tube 20. The thickness of the annular gap will depend, inter alia, upon suture size (e.g., suture sizes 9-0 to 2), suture type, etc. The tubular sleeve 60 is mounted to the distal end 22 of tube 20, such that the slits 35 (or other equivalent embodiments of collapsible end 23) are contained within axial passage 66 of tube 60. Tube 60 is mounted using conventional mounting methods including mechanical fasteners, adhesives, bonding agents ultrasonic welding, and the like.

Plug 50 is seen to be, preferably, a cylindrical member, preferably solid, having proximal end 54 and distal end 52. The outer diameter of cylindrical plug 50 is sized to have an inner diameter less than the inner diameter of tube 20 and sufficiently large to effectively fit into the distal end 22 of tube 20, thereby effectively preventing the distal end section 23 from collapsing. Plug 50 in alternative, equivalent embodiments may have various configurations including conical, polyhedral and the like. More than one plug 50 may be used if desired. It is preferred that plug 50 have a length substantially equal to the length of distal end section 23 although this is not required.

Mounted to the tube 20 distal to the proximal end 26 is the optional adapter 70. The adapter 70 is seen to have a rectangular, flat plate member 75 with a central hole 77 extending therethrough. A tapered collar 80 is seen to extend distally about the central hole 77. A proximal collar 90 is seen to extend proximally about the central hole 77. Rectangular flat plate member 75 is seen to have tab members 85 extending distally on either side of tapered collar 80. The purpose of tab members 85 is to mount to a conventional trocar cannula. The adapter 70 is mounted to the tube 20 using conventional mounting techniques including mechanical fasteners, adhesives, bonding agents, ultrasonic welding and the like.

Also seen in FIGS. 1, 2, 3 and 4 is a suture 150 having a conventional surgical needle 170 affixed to the distal end 151. The suture 150 is seen to have pre-tied knots 155 and 160. The suture 150 has distal end 151 and free proximal end 152.

The sutures 150 which can be used with the tube knot applicators 10 of the present invention include conventional absorbable and non-absorbable sutures and equivalents thereof. The non-absorbable sutures may include nylon, polypropylene, polyester, silk and the like and equivalents thereof. The absorbable sutures include polydioxanne, gut, polyglycolides and the like and equivalents thereof. The surgical needles 170 which may be used with the tube knot applicators 10 include conventional surgical needles such as curved, straight, compound curved and straight and the like made from surgical grade alloys including stainless steel, and the like and equivalents thereof.

The knots 155 and 160 are conventional, known surgical knots and equivalents thereof. Specifically, knot 155 is a conventional surgical slip knot. Knot 160 is a conventional surgeon's locking knot. Knot 155 is tied in a conventional manner. For example, two loops 156 are formed side-by-side with substantially equal diameters. The end of the second loop 156 is passed over and then through both loops 156. One or more loops 156 may be used to form slip knot 155. Similarly one or more slip knots 155 may be use with tube knot applicator 10.

Knot 160 is tied in the following manner. The end of the second loop 156 after being passed through each loop 156 is formed into a third loop 161 and a simple half hitch is made.

Figure 3:
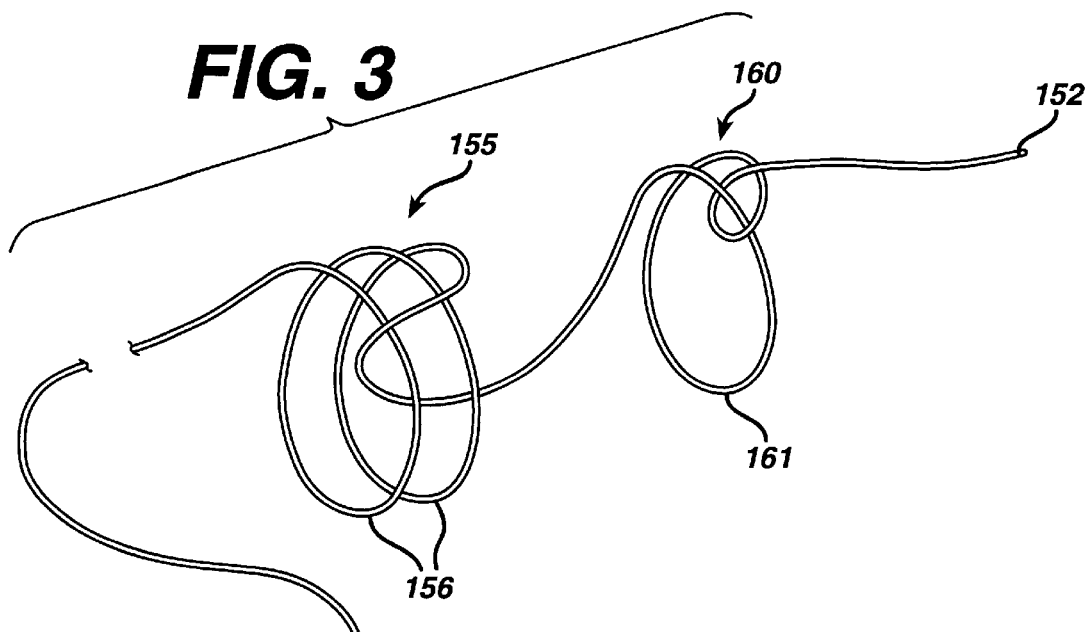
FIG. 3 is a perspective view of a suture used in the tube knot applicator of the present invention having two loops and two knots; a surgical needle is mounted to the distal end.
Figure 4:
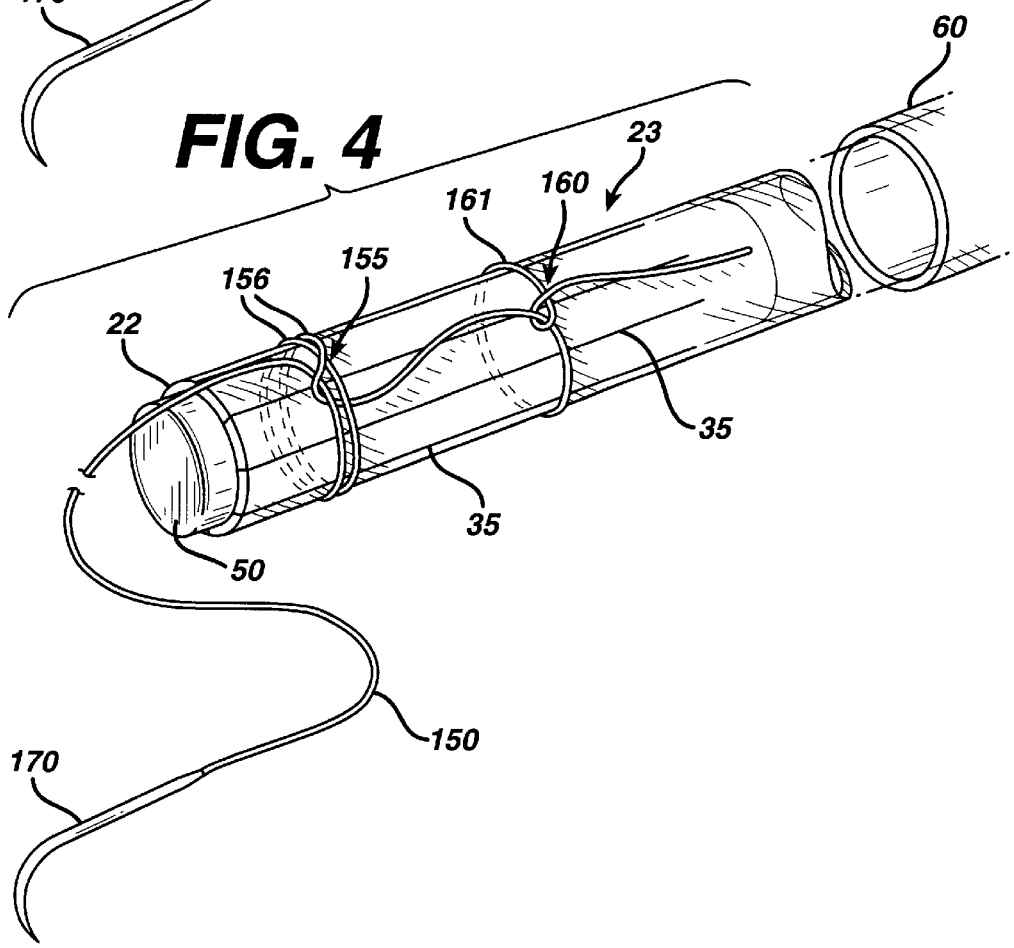
FIG. 4 is a partial perspective view of the distal end of the tube knot applicator of the present invention having the suture loops of FIG. 3 mounted over the distal end of the tube before the outer sleeve is placed over the loops and knots and the distal end of the tube.

The tube knot applicator 10 is assembled with suture 150 having surgical needle 170 mounted to distal end 151 in the following manner. The tubular sleeve 60 is slid onto the tube 20 proximal to collapsible distal section 23. Then plug member 50 is inserted into the distal end 23 of tube 20 such that the distal end section 23 is in an uncollapsed configuration. Then, as seen in FIG. 3 and FIG. 4, knots 155 and 161 are tied in suture 150 about the end section 23 forming loops 156 and 161. If desired, knots 155 and 160 may be tied prior to mounting the loops 155 and 160 about the collapsible end section 23. In addition more than one slip knot 155 and more than one locking knot 160 may be used. Next, the tubular sleeve member 60 is slid distally over the loops 155 and 160 and over the end section 23. Sleeve member 60 is secured to tube 20 using conventional techniques including adhesives, mechanical fasteners and the like. If desired, a conventional trocar cannula adaptor plate 190 may be mounted to the tube 20. A distal length of suture 150 having needle 170 attached to end 151 is seen to extend distally from annular space 68. If desired, although not preferred, sleeve member 60 may be eliminated with the suture loops and knots being mounted in a similar manner, and the applicator would be used in a similar manner to that described below.

The tube knot applicator 10 is made from conventional bicompatible material and equivalents thereof. For example, the tube 20 and the sleeve 60 may be made from polyethylene, polypropylene, polyester, polyether and the like and combinations thereof. The plug member 50 may be made from materials such as elastomeric rubber, latex and other polymeric materials and the like. If desired, the tube knot applicator 10 could be made from metals such as stainless steel and the like.

FIGS. 5–15 illustrate the use of the tube knot applicator 10 of the present invention in an endoscopic procedure. Referring first to FIGS. 5–7, an endoscopic needle grasper 200 is inserted into the proximal end 26 of tube 20 a sufficient distance to effectively push the cylindrical plug member 50 out from the distal collapsible end section 23 of the tube 20. The distal slotted end section 23 is prevented from collapsing due to the presence of the distal end 205 of the needle grasper 200 within passage 30 of the distal end section 23. Referring next to FIG. 6, prior to inserting the needle grasper 200 into the proximal end 26 of tube 20, the proximal end 44 of resilient sleeve 40 is displaced distally about the proximal end 26 and over and onto itself. Then, after the shaft 201 of the needle grasper 200 has been inserted and positioned within tube 20 and needle 170 has been grasped by needle grasper 200, the folded over end 44 is displaced proximally and forms a resilient seal with the shaft 201 of the needle grasper 200. It is known that endosurgical instruments typically require seals to prevent the escape of an insufflation gas which is used to insufflate a body cavity. The sleeve 40 also serves to frictionally engage and maintain the grasper 200 in a fixed position with respect to tube 20. However, the frictional force may be overcome when the surgeon applies an axial force upon the grasper 200 thereby allowing the surgeon to easily move the grasper 200. As mentioned previously, referring to FIG. 7, the distal end 205 of the needle grasper 200 prevents distal end section 23 of tube 20 from collapsing.

Figure 8:
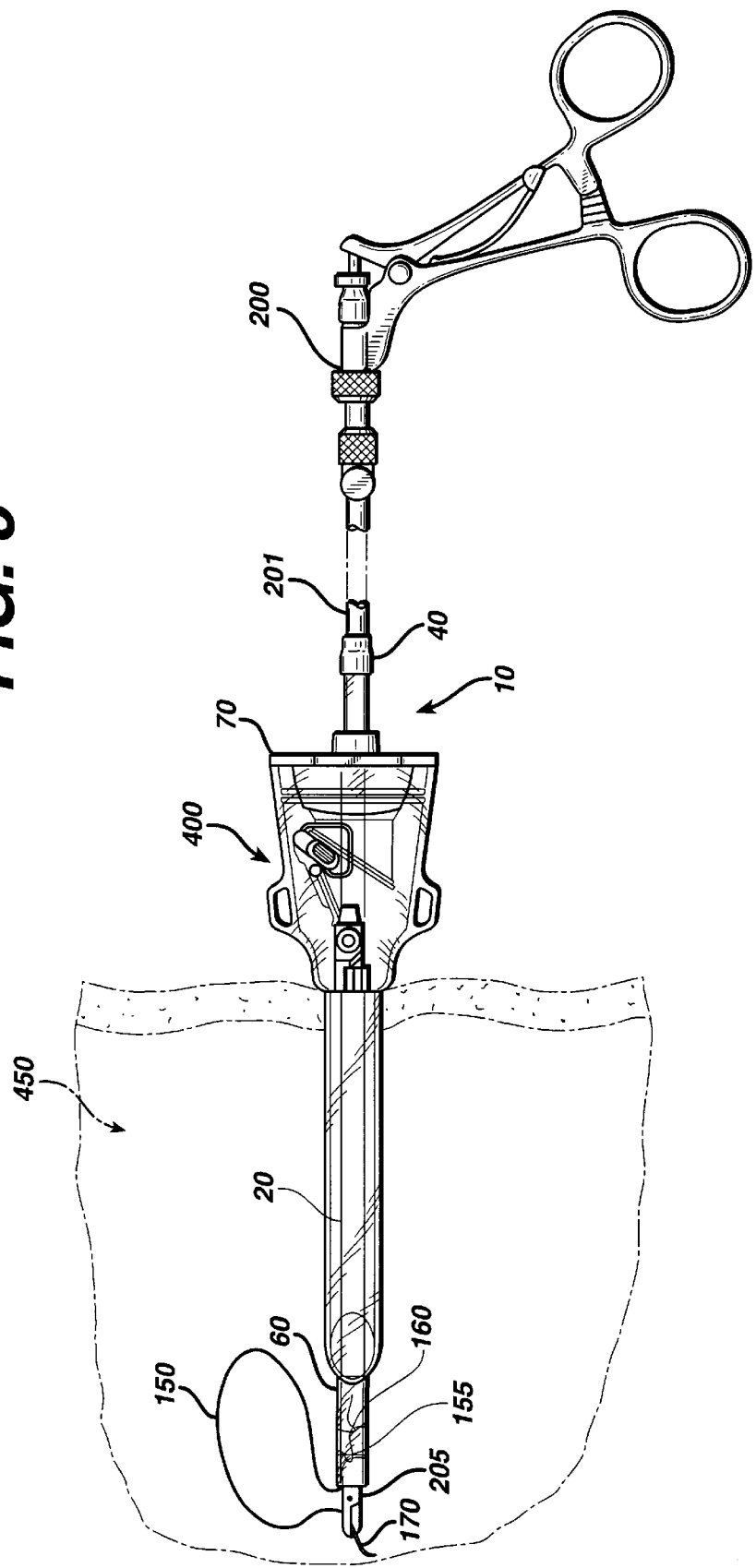
FIG. 8 is a side view of the tube knot applicator of the present invention inserted through a conventional trocar cannula into a body cavity and further showing in a partial cut-away view a needle grasper extending through the tube knot applicator and into a body cavity while grasping a surgical needle mounted to the distal end of a suture mounted in the tube knot applicator.

The tube knot applicator 10 is now ready for insertion into the body cavity of a patient. This is typically done as seen in FIG. 8 through a conventional trocar cannula 400 which has been placed into a body cavity 450 of a patent using a conventional trocar obturator. The trocar adaptor plate 70 is seen to lock into the proximal end of a trocar cannula 400.

Referring now to FIGS. 9–11, after the distal ends 11 and 205, respectively, of the tube knot applicator 10 and the needle grasper 200 have been positioned proximate to tissue 300 having incision 310 which is to be sutured, the surgeon maneuvers the needle 170 and pushes it through the tissue 300 about the incision 310 and out of the tissue 300 thereby pulling suture 150 through the tissue about the wound 310.

Figure 12:
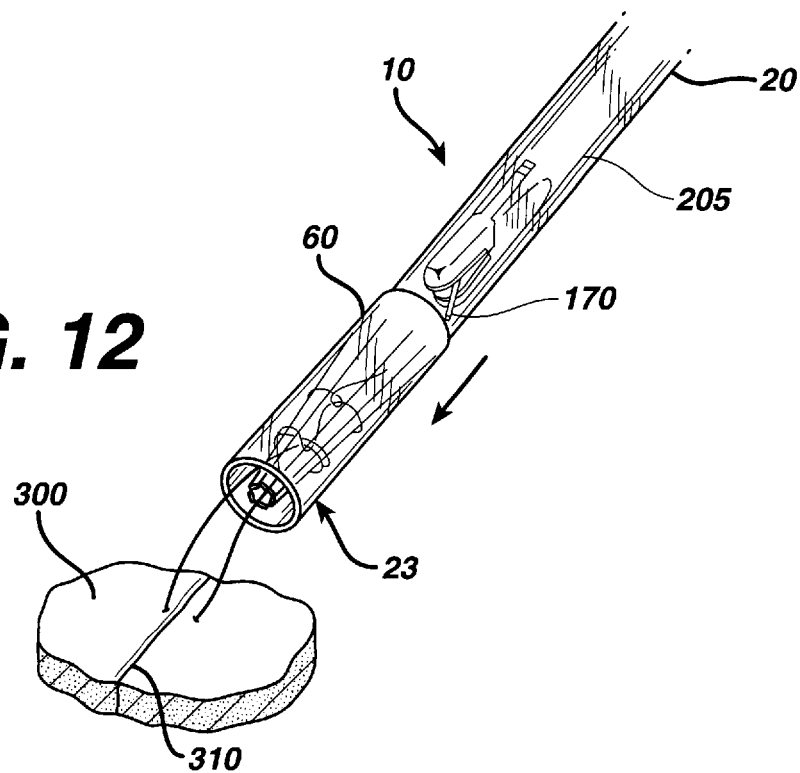
FIG. 12 is a partial perspective view of the distal end of the applicator showing the needle grasper withdrawn proximally into the tube allowing the distal end of the tube to assume a collapsed configuration thereby allowing the suture loops and knots to slip off of the distal end of the tube onto the suture strand thereby automatically knotting the suture.
Figure 13:
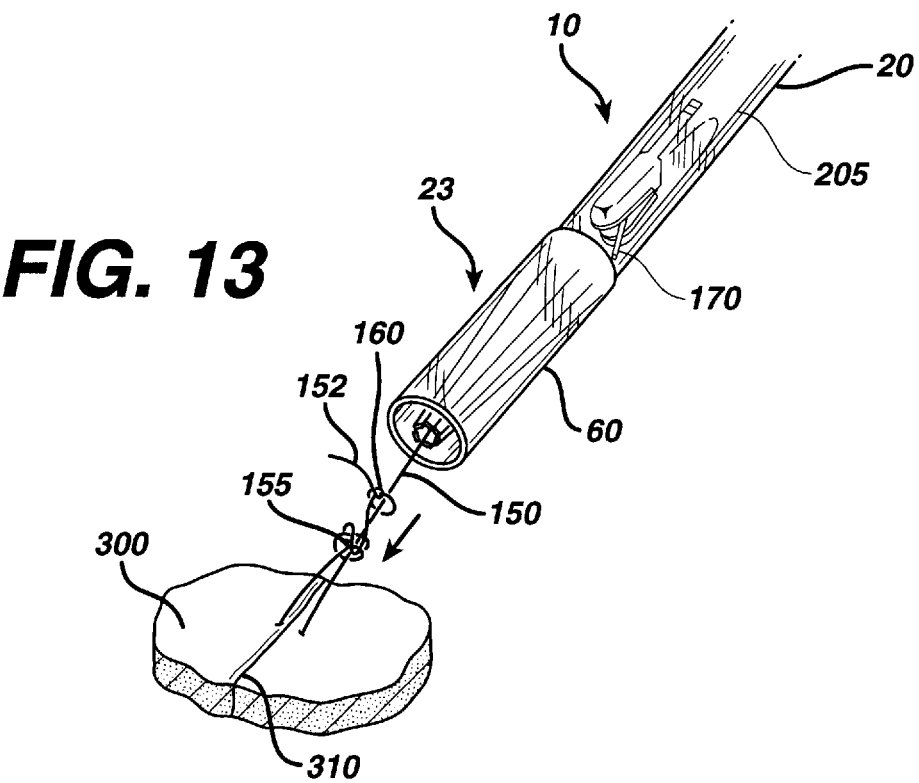
FIG. 13 is a partial perspective view of the tube knot applicator showing the distal end collapsed and the knots in a position distal to the distal end of the tube knot applicator and moving toward the incision in the tissue.
Figure 14:
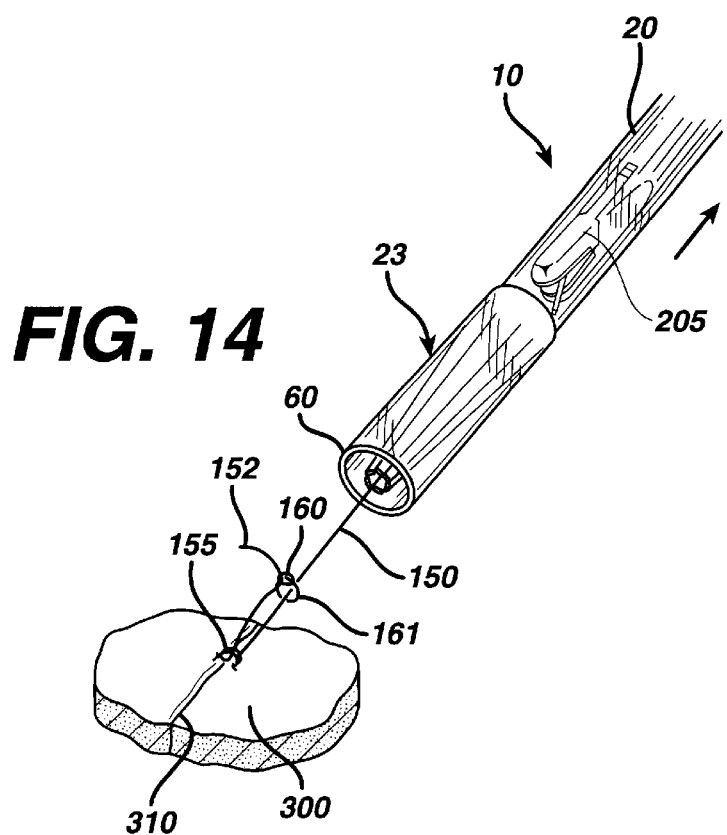
FIG. 14 is a partial perspective view of the tube knot applicator showing the slip knot tightened adjacent to the incision and the locking knot in a position proximal to the slip knot.
Figure 15:
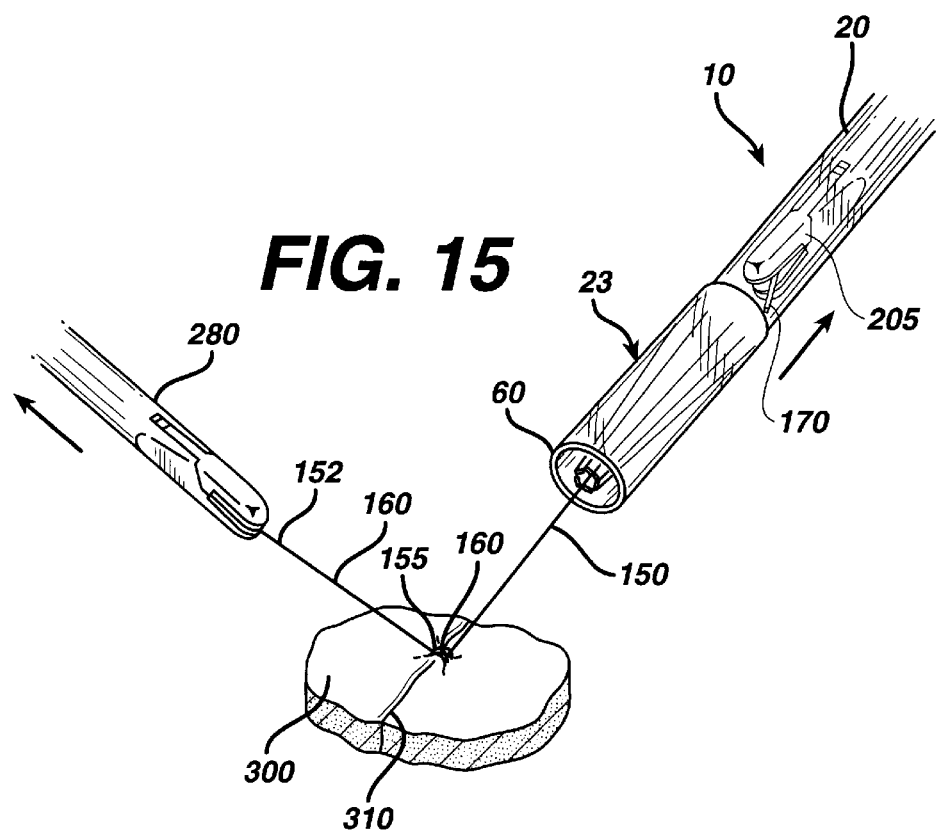
FIG. 15 is a partial perspective view showing a second needle grasper pulling the proximal free end of the suture causing the knots to tighten about the incision in the tissue as the first needle grasper pulls on the needle attached to the other end of the suture.

Next, as seen in FIG. 12, the distal end 205 of the needle grasper 200 with needle 170 is displaced proximally into the tube 20 (proximal to the distal section 23) thereby allowing the distal section 23 to collapse and allowing the loops 156 and 161 and knots 155 and 160 to slide distally off of the collapsed distal end section 23. As seen in FIG. 13, the surgeon next continues to pull distally on needle grasper 200 while holding the tube 20 steady, so that the grasper 200 moves proximally with respect to the tube 20 and section 23 with slots 35. This causes the loops 156 and 161 and knots 160 and 155 to slip onto the suture 150 as they slip off of the distal end section 23. The grasper 200 is continually pulled distally causing the slip knot 155 and locking knot 160 to tighten. In FIG. 15, a second needle grasper 280 is inserted into the patient's body cavity 450. The free end 152 of suture 150 is pulled proximally by the grasper 280 while the surgeon continues to pull needle 170 and distal end 151 of suture 150 proximally with grasper 200 thereby tightening the slip knot 155 and locking knot 160 in suture 150 about the wound 310. The needle 170 and excess suture are cut from suture 150, leaving a knotted suture about incision 310.

Figure 16:
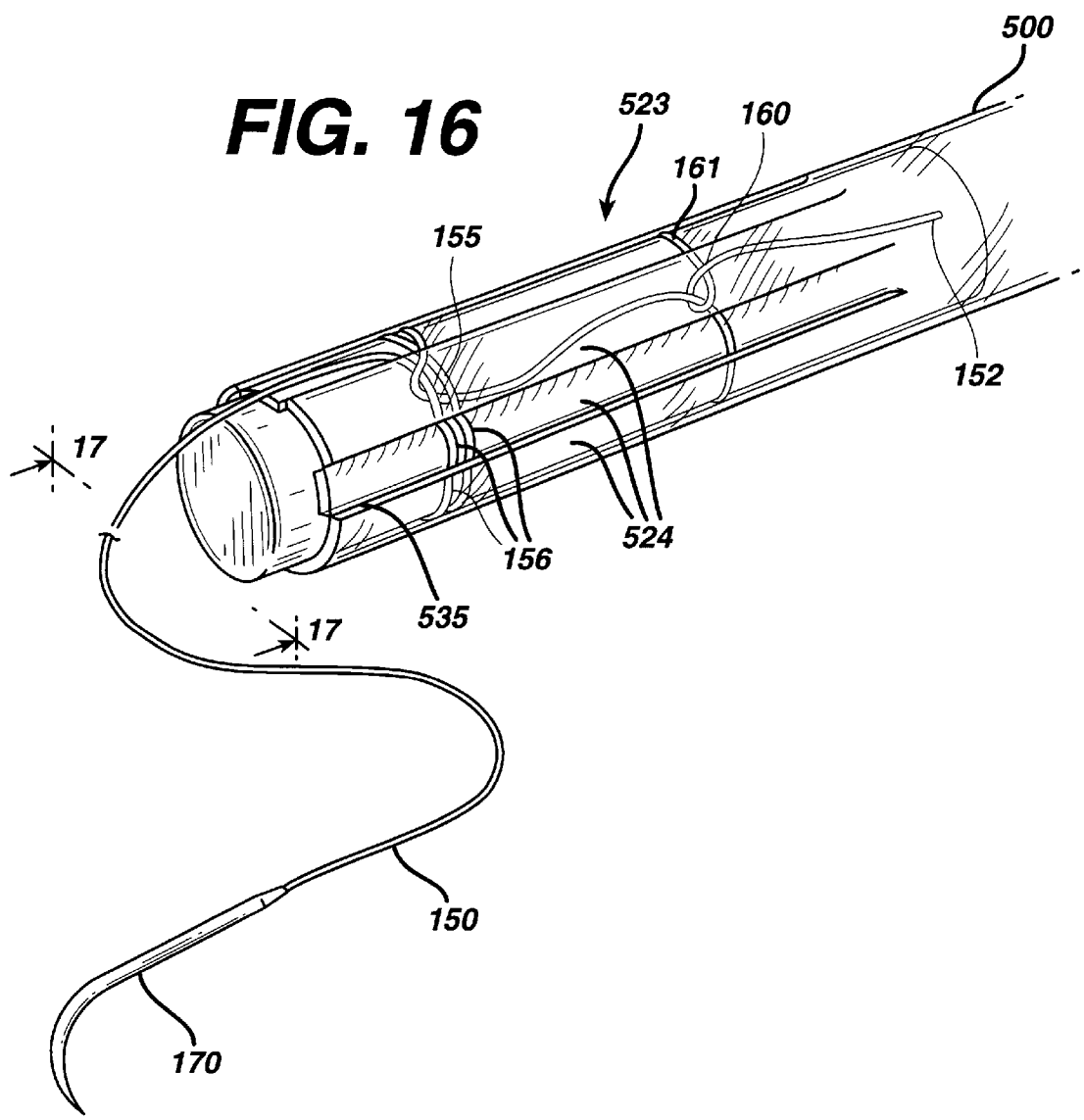
FIG. 16 is a partial perspective view of the distal end of an alternate embodiment of the tube knot applicator of the present invention.
Figure 17:
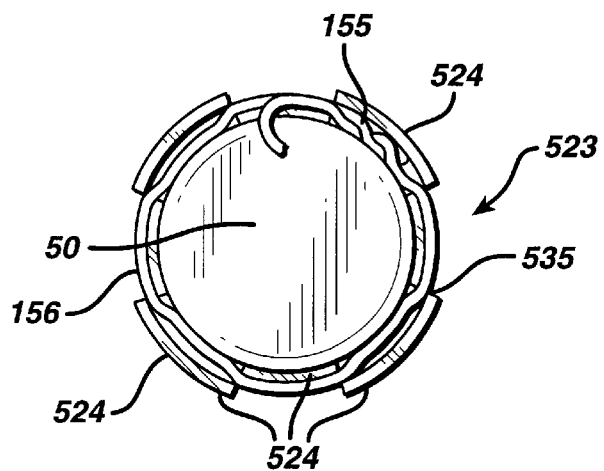
FIG. 17 is an end view of the embodiment of FIG. 16 taken along View Line 17—17.

An alternate embodiment of the tube knot applicator 10 is illustrated in FIGS. 16 and 17. A partial perspective view of a slotted distal end 523 extending from tube 500 is seen. The suture 150 and loops 156 and 161 along with slip knot 155 and locking knot 160 are woven through the slots 535 of distal end section 523. In this manner the slotted members 524 act partially as a tubular sleeve and thus no tubular sleeve 60 is required in this embodiment. The slotted members 524 may be of equal widths or of varying widths. All other aspects of the tube knot applicator would remain the same as tube knot applicator 10. If desired, the suture 150 and loops 156 and 160 as well as knots 155 and 160 do not have to be woven through the slots 535, but may be mounted about slotted distal end 535.

The following example is illustrative of the principals and practice of the present invention although not limited thereto.

EXAMPLE

A patient is prepared for an endosurgical procedure using conventional endoscopic surgical techniques. The patient is anesthetized with a sufficient dose of a conventional anesthesia to induce an effective anesthetized state. The patient is intubated with an endotracheal tube and ventilated as required with a conventional ventilator apparatus. The patient's abdominal cavity is insufflated using a conventional Veres needle which is attached to a conventional insufflator device which maintained patient's abdominal cavity in a state of pneumoperitoneum. Five conventional trocars are inserted into the patient's abdominal cavity. The trocar obturators are removed from the trocar cannulas leaving the trocar cannulas as pathways to the abdominal cavity. An endoscope is inserted into one of the trocar cannulas and connected to a conventional endoscopic video display. An incision is made into a section of muscle tissue in the abdominal cavity using conventional endoscopic cutting instruments. Next, the endoscopic tube knot applicator 10 of the present invention is prepared for use by inserting a conventional endoscopic needle grasper 200 into the proximal end of the tube 20 of the applicator 10. Prior to inserting the distal end of the needle grasper 200 into the proximal end of the tube 20, the resilient sleeve 40 is rolled back upon itself. The needle grasper is inserted through the internal passage 30 of tube 20 until the plug 50 is pushed out of the distal end section 23 and the distal end of the needle grasper 200 extends beyond distal end 22 of the tube 20. The needle 170 is then grasped by the jaws of the needle grasper 200. Next the resilient sleeve 40 is displaced proximally such that the sleeve forms a seal with the needle grasper shaft 201 and effectively prevents the needle grasper from moving inadvertently with respect to the tube 20. Next, the tube knot applicator 10 and the needle grasper 200 are inserted through a conventional trocar cannula 400 which has been placed into a body cavity 450. Adaptor plate 70 is locked into trocar cannula 400. After the distal ends of the tube knot applicator 10 and the needle grasper 200 have been positioned proximate to tissue 300 which is to be sutured, the surgeon maneuvers the needle 170 and pushes it through the tissue 300 about the wound 310 and out of the tissue 300 thereby pulling suture 150 through the tissue about the wound 310.

The distal end 205 of the needle grasper 200 holding the needle 170 is then displaced proximally into the tube 20, proximal to the distal section 23, thereby allowing the distal section 23 to collapse and allowing the loops 156 and 161 and knots 155 and 160 to slide distally off of the collapsed distal end section 23 of the tube knot applicator and onto suture 150. The surgeon then continues to pull distally on the needle grasper 200 while holding the tube 20 steady so that the grasper 200 moves proximally with respect to the tube 20. This causes the loops 156 and 161 and knots 155 and 160 to slip distally on the suture 150 after they have slipped off of distal end section 23. The grasper 200 is pulled further distally causing the slip knot 155 and locking knot 160 to slide and tighten. A second needle grasper 280 is inserted into the patient's body cavity 450 through a trocar 400. The free end 152 of suture 150 is pulled proximally by the grasper 280 while the surgeon continues to pull the needle 170 and distal end 151 of suture 150 proximally with grasper 200 thereby further tightening the knots 155 and 160 in the suture about the wound 310. The needle 170 and excess suture 150 are cut from suture 150, leaving a knotted suture about incision 310. The needle 170 and excess suture 150 are then removed, the trocars 400 are removed along with the endoscope and the incisions caused by the trocars 400 are closed in accordance with conventional procedures.

The tube knot applicator of the present invention has many advantages. The advantages include the capability of intracorporeally knotting pre-tied sutures. In addition, the tube knot applicator device 10 has the capability of simultaneously applying two knots; it is believed that this has previously not been possible. In addition, the use of the device 10 in an endosurgical procedure eliminates the need for a separate or additional trocar cannula for a needle grasper instrument.

Although this invention has been shown and described with respect to detailed embodiments thereof, it will be understood by those skilled in the art that various changes in form and detail thereof may be made without departing from the spirit and scope of the claimed invention.

What is claimed is:

1. A surgical suture knot applicator, comprising:
   a tube having a distal end, a proximal end and an axial passage therethrough, the tube having an inner surface and an outer surface, the tube having a constant diameter;
   means for collapsing the distal end of the tube, wherein said collapsing means may be engaged or disengaged, said collapsing means comprising at least two longitudinal slots in the distal end of the tube, and wherein the distal end collapses to a diameter less than the uncollapsed diameter;
   engagement means for engaging or disengaging the collapsing means, said engagement means mounted in the distal end of the tube, said engagement means comprising a plug member slidably mounted in the distal end of the tube;
   a tubular sleeve having an inner surface and an outer surface mounted over the distal end of the elongated member;
   a surgical suture mounted to the distal end of the tube over the collapsing means;
   a surgical needle mounted to the suture; and,
   at least one pre-tied knot in the suture, the knot mounted on the distal end of the tube between the outer surface of the tube and the inner surface of the tubular sleeve.

2. The applicator of claim 1 further comprising a trocar cannula adapter having a hole therethrough wherein the adaptor is mounted to the tube.

3. The applicator of claim 1 further comprising sealing means mounted to the proximal end of the tube.

4. The applicator of claim 1 wherein the plug member comprises a cylinder.

5. The applicator of claim 1 wherein the tube has a rectangular cross-section.

6. The applicator of claim 1 wherein the tube has a polyhedral cross-section.

7. The applicator of claim 1 additionally comprising means for engaging and holding a needle grasper mounted to the proximal end of the tube.

8. The applicator of claim 1 wherein the knot is a slip knot.

9. The applicator of claim 1 wherein the knot is a locking know.

10. The applicator of claim 1 comprising at least one slip knot and at least one locking knot.

11. A surgical suture knot applicator, comprising; a tube having a distal end, a proximal end and an axial passage therethrough, the tube having an inner surface and an outer surface, the tube having a constant diameter;
    means for collapsing the distal end of the tube, wherein said collapsing means may be engaged or disengaged, said collapsing means comprising at least two longitudinal slots in the distal end of the tube, and wherein the distal end collapses to a diameter less than the uncollapsed diameter;
    engagement means for engaging or disengaging the collapsing means, said engagement means mounted in the distal end of the tube, said engagement means comprising a plug member slidably mounted in the distal end of the tube;
    a surgical suture mounted to the distal end of the tube over the collapsing means;
    a surgical needle mounted to the suture; and,
    at least one pre-tied knot in the suture, the knot mounted on the distal end of the tube.

12. The applicator of claim 11 further comprising a trocar cannula adapter having a hole therethrough wherein the adaptor is mounted to the tube.

13. The applicator of claim 11 further comprising sealing means mounted to the proximal end of the tube.

14. The applicator of claim 11 wherein the plug member comprises a cylinder.

15. The applicator of claim 11 wherein the tube has a rectangular cross-section.

16. The applicator of claim 11 wherein the tube has a polyhedral cross-section.

17. The applicator of claim 11 additionally comprising means for engaging and holding a needle grasper mounted to the proximal end of the tube.

18. The applicator of claim 11 wherein the knot is a slip knot.

19. The applicator of claim 11 wherein the knot is a locking knot.

20. The applicator of claim 11 comprising at least one slip knot and at least one locking knot.

* * * * *